United States Patent [19]
Brenner et al.

[11] 3,971,852
[45] July 27, 1976

[54] PROCESS OF ENCAPSULATING AN OIL AND PRODUCT PRODUCED THEREBY

[75] Inventors: Joseph Brenner; Gary H. Henderson, both of Middletown; Robert W. Bergensten, Kerhonkson, all of N.Y.

[73] Assignee: Polak's Frutal Works, Inc., Middletown, N.Y.

[22] Filed: June 12, 1973

[21] Appl. No.: 369,306

[52] U.S. Cl. ................................. 426/103; 8/79; 252/316; 252/522; 424/34; 424/35; 424/49; 426/89; 426/102; 426/650; 428/307
[51] Int. Cl.² .................... A23L 1/06; A61K 7/46; B01J 13/02
[58] Field of Search ........................ 252/316, 522; 117/100 A; 424/35; 426/89, 96, 650, 103

[56] References Cited
UNITED STATES PATENTS

| | | | |
|---|---|---|---|
| 2,886,446 | 5/1959 | Kramer et al. | 426/89 X |
| 2,897,119 | 7/1959 | Dunn | 424/35 X |
| 3,091,567 | 5/1963 | Wurzburg et al. | 424/35 |
| 3,565,559 | 2/1971 | Sato et al. | 252/316 X |
| 3,686,701 | 8/1972 | Charle et al. | 252/316 X |

*Primary Examiner*—Richard D. Lovering
*Attorney, Agent, or Firm*—William S. Alexander

[57] ABSTRACT

Compositions, preferably in particulate form, comprising a cellular matrix having oil in the cells thereof in which the matrix comprises polysaccharide and polyhydroxy compounds in such proportions that the oil may constitute up to 80% by volume so stably held in the cells that the extractable oil is not substantially in excess of 5%. This is accomplished by proportioning the ingredients to produce a glassy, preferably water soluble, matrix having a plastic or flowable range that prevents or seals oil escape paths in the wall material such as cracks, fissures, pin holes and deep pits. The polysaccharides are primarily not the sweet, readily soluble saccharides like sugar but rather higher polysaccharides of the non-sweet, colloidally soluble types such as natural gums, e.g., gum arabic, starch derivatives, dextrinized and hydrolyzed starches, and the like. The polyhydroxy compounds may be alcohols, plant-type sugars, lactones, monoethers and acetals. The process of making these compositions comprises forming an aqueous phase of the polysaccharide and polyhydroxy compound in proper proportions, with added emulsifier if necessary or desirable, emulsifying the oil (either of the volatile or non-volatile type) in the aqueous phase and removing moisture while the mass is plastic or flowable, e.g., by spray drying droplets of the emulsion, by spreading on a substrate such as a belt, drum, drinking cup and the like.

12 Claims, 13 Drawing Figures

PROCESS OF ENCAPSULATING AN OIL AND PRODUCT PRODUCED THEREBY

INTRODUCTION

The present invention relates to a novel composition of matter, usually in particulate form, and a process for producing the same. More particularly when the composition is in particulate form it comprises generally spherical capsules, usually less than 400 microns in diameter. Regardless of the form in which the product is prepared, it comprises a glassy solid cellular matrix, usually water soluble but sometimes deliberately not readily soluble, e.g., of a polysaccharide and a polyhydroxy compound, having oil droplets, in many cases of about 1 micron diameter, in the cells dispersed therethrough in a proportion that may be limited only by the maximum oil content that can be maintained in the internal phase of an emulsion from which the solid state product is produced by removal of moisture. In practice the oil content of the product is limited to a maximum of about 80% by volume. The product is produced by converting the emulsion of oil droplets in a solution of the matrix ingredients to the solid state with removal of moisture largely if not entirely while the matrix is at least plastic. Where the product is particulate, the particles or capsules are preferably produced by a spray drying process characterized by high recovery of the oil in the capsules which have low extractable oil upon exposure to non-polar extracting liquids.

BACKGROUND OF THE INVENTION

Many proposals have been made to encapsulate core materials that require protection until time of use in a protective covering. Cf. Nack, Microencapsulation Techniques, Soap and Sanitary Chemicals, Vol. 21, pp 85–98, Feb. 4, 1970. Among process for making somewhat globular capsules that have been described in the technical literature and patents are coacervation and spray drying.

The coacervation process generally involves three steps: (1) formation of three immiscible chemical phases, a liquid manufacturing vehicle phase, a core material phase that can be dispersed or emulsified in the vehicle phase, as droplets, and a coating material phase, (2) depositing the coating material phase around the droplets of the core material phase and (3) rigidizing the coating to form the self-sustaining particles. The typical resulting particle is a globule of core material surrounded by a wall of coating material. Size may vary from about 5 to 5,000 microns. The core material may be liberated by mechanically breaking the outer wall by external or internal force, by degradation of the outer wall by melting, decomposition or dissolving or by diffusion of the core material through the wall. Particles produced by this method have found successful application in a number of industries, e.g., coated duplicating papers and sustained release drugs, but have not been widely accepted for flavors and fragrances in the food and cosmetic industry because they are relatively expensive and not rapidly soluble in water, Cf. Bakan, Microencapsulation as Applied to Pharmaceutical Products, Eastern Regional IPT Section, Academy of Pharmaceutical Sciences, Philadelphia, Pa., Oct. 4, 1968.

In the spray drying process particles are produced by a three step Operation comprising (1) forming an emulsion of the liquid core material in a solution, usually aqueous, of the normally solid coating material and (2) breaking up the emulsion into droplets of desired size, e.g., in a spray nozzle, from a spinning disc, or apertured centrifugal atomizer, and (3) removing moisture in a drying environment to solidify the coating material in the droplets to form solid particles. The drying environment may be hot drying air, e.g., in a spray drying tower, a dehydrating liquid, e.g., propylene glycol; a bed of dehydrating powder, e.g., dry starch powder; or the like. The particles produced by this process, while they may be of various sizes and shapes and may be "hollow" or "solid", are characterized by cellular structure comprising many dispersed globules of the core material in a matrix of the coating material. "Solid" in this context means that a particle has more or less uniform structure throughout, as opposed to the "hollow" form of particle which has a shell surrounding a void, but it does not imply absence of pores or cells in the body thereof. Particles or capsules produced by this method have been used commercially in many applications, including foods where the core material is a flavoring oil and cosmetics where the core material is a fragrance oil. Cf. Balassa, Microencapsulation in the Food Industry, CRC Critical Review Journal in Food Technology, July 1971, pp 245–265; Barreto, Spray Dried Perfumes for Specialties, Soap and Chemical Specialties, December 1966; Maleeny, Spray Dried Perfumes, Soap and San Chem, Jan. 1958, pp 135 et seq.; Flinn and Nack, Advances in Microencapsulation Techniques, Batelle Technical Review, Vo. 16, No. 2, pp 2–8 (1967); Merory, Food Flavorings, Avi Pub. Co. (1960), pp 274–277.

One of the best of the known processes for producing microcapsules involves spraying into a drying atmosphere globules or droplets of an emulsion or solution containing, in a continuous aqueous phase, a hydrophilic colloid such as dextrin or gum Arabic as the coating material, with the addition if necessary of an emulsifier, and a volatile or non-volatile core material of organic liquid, hereafter sometimes referred to as oil or oils, in a dispersed phase. The products of this process are dry, somewhat porous powders consisting of roughly spherical, convoluted particles with the coating material in the solid state and with the organic liquid either dispersed as minute droplets throughout the particle, or dissolved in a solid matrix, or both, depending on the compatibility of the oil and coating material.

In the conventional spray drying process of producing capsules the surface of the sprayed globule of the emulsion dries to form a solid outer crust almost immediately on contact with the drying atmosphere and further evaporation of entrapped moisture normally causes the particle to shrink, forming craters and cracks in the crust.

Capsule manufacture by this process of spray drying has been accompanied by loss of considerable proportions of oil by evaporation during spray drying and the capsules produced have been characterized by relatively high extractable oil. The maximum practical proportion of oil to wall material that can be used in the emulsion is usually limited (1) by factors inherent in the mixture, particularly the ability of the aqueous phase to hold oil as the dispersed phase, and (2) by the losses in processing. These practical considerations have limited the oil to a fraction of the highest proportion the particles theoretically are capable of containing and such oil as is originally encapsulated can gradually escape from the dry particle, perhaps by diffusing through the relatively porous, cracked and cratered wall material. A quick test of the potential loss during storage may be made by determining, in the manner hereinafter described, the percent "extractable oil". While the mechanism of the oil losses has not been fully established, both modes of oil loss, i.e., the loss during spray drying and during storage, may be due to the relatively poor barrier afforded by the walls of the particles produced by conventional spray drying procedure using conventional wall materials.

SUMMARY OF THE INVENTION

It has now been discovered, quite unexpectedly, that significant advantages and benefits are achieved by using combinations of matrix forming materials characterized by (1) the ability of forming the continuous phase of an emulsion in which a high proportion of oil can be held in the dispersed phase, and (2) plasticity or flowability in the drying temperature range during which a solid is derived from the emulsion by removal of moisture, e.g., when the emulsion is converted into particles by a spray drying procedure. The particles or capsules obtained by spray drying such an emulsion are largely spherical without substantial oil escape paths in the wall formed from the dissolved combination of matrix forming solids in the continuous phase of the emulsion due to discontinuities such as craters or pits, cracks, fissures, pin holes and the like. The result is high oil recovery and low extractable oil content.

The practical upper limit of oil in the solid matrix is obtained by properly removing moisture from an emulsion having the maximum oil content that can be maintained in the dispersed phase. This oil content varies somewhat in different combinations of the matrix forming material but the maximum content for any particular combination is easily determined by observation of the mixture which undergoes a phase inversion when the oil content thereof is increased above this maximum limit.

The matrix resulting from removal or moisture from the emulsion, whether in the form of a sheet, block or particles, appears to have a glassy, amorphous cellular structure characteristic of materials that remain in liquid phase during moisture removal and solidify without substantial subsequent shrinkage. The body of the matrix in section is a honeycomb of spherical cavities or cells holding tiny globules of oil that may be of the order of one micron in diameter, although other diameters are obtainable by varying the technique of forming the emulsion.

One combination of matrix forming materials which gives these unexpected, new results comprises mixtures of polysaccharides and polyhydroxy compounds as hereinafter defined which form with the oil emulsions that (a) have a plastic or flowable state over a substantial range of temperature that is in a critical range over which water is readily removed between the fully liquid and fully solid states, (b) form a surface that selectively permits removal of water and (c) become, on removal of moisture, a cellular matrix of the polysaccharide and polyhydroxy materials in solid state with oil fixed in the cells thereof. Materials other than polysaccharides and polyhydroxy compounds that, in combination, satisfy criteria (a), (b) and (c) may be substituted for part or all of one or both of these materials. The invention includes the novel product and the process of producing the same.

DETAILED DESCRIPTION OF THE INVENTION

The novel composition and process of producing the same will be described in conjunction with the drawings in which.

The polysaccharides employed in admixture with polyhydroxy compounds in products of the invention are solids characterized by solubility in water and by at least partial solubility in, or capability of at least partially dissolving, the polyhydroxy compound within the ranges of proportions used. They are primarily not the sweet, readily soluble saccharides like sugar but higher polysaccharides that may be natural, such as gum arabic and similar vegetable gums, or synthetic, such as degradation and modified products of starch, which usually form colloidal solutions. Certain starch degradation products such as dextrinized starch which are suitable polysaccharides for use in the invention contain a wide spectrum of saccharides of different molecular weights including a sufficient proportion in the polysaccharide molecular weight range to be good encapsulants and varying proportions of lower saccharides such as mono-, di- and trisaccharides which are polyhydroxy compounds, as later defined. When such polysaccharides are used it may be necessary to make adjustments in the proportion of added polyhydroxy compound in order to obtain the proper balance of polysaccharide and polyhydroxy compounds to assure proper melt characteristics as later described since the proportion of lower saccharides in the starch degradation products, while usually too low to satisfy the requirements of the invention for polyhydroxy compound, may be large enough to affect significantly the amount of added polyhydroxy compound required to obtain the said proper proportion of polyhydroxy compound to polysaccharide in the product.

Among the polysaccharides that may be used are dextrins derived from ungelatinized starch acid esters of substituted dicarboxylic acids represented diagrammatically by the formula:

in which R is a radical selected from the class consisting of dimethylene and trimethylene and $R^1$ is a hydrocarbon substituent of R selected from the class consisting of alkyl, alkenyl, aralkyl and aralkenyl groups. These ungelatinized starch-acid esters are prepared by reacting an ungelatinized starch, in an alkaline medium, with a substituted cyclic dicarboxylic acid anhydride having the following formula:

in which R and $R^1$ represent the so designated substituent groups just defined. Examples of such anhydrides are the substituted succinic and glutaric acid anhydrides. Such a polysaccharide will be referred to hereinafter as polysaccharide X.

Other useful polysaccharides include products derived from dextrinized starch which will be referred to hereinafter as polysaccharide Y and hydrolyzed starch which will be referred to hereinafter as polysaccharide Z. In general these products contain minor proportions of lower saccharides such as dextrose and it is customary to classify them as to sweetness by a dextrose equivalent (DE) rating, number or range which for solids (as opposed to syrups) is in the approximate range of 10 – 25, although some manufacturers produce solid products having higher DE ratings for several purposes in the food field, e.g., ice cream and other frozen desserts, cake toppings, cream substitutes, confections and the like.

The polysaccharide content may comprise a single polysaccharide or mixture of two or more polysaccharides as illustrated hereinafter.

The polysaccharide should possess emulsifying properties either inherently or by reason of the presence of a minor proportion of a suitable emulsifying agent. Further definition of emulsifying agents is unnecessary because they are well known to those skilled in the art. Examples of satisfactory emulsifying agents are sodium diisooctyl sulfosuccinate and sodium caseinate. If emulsifying agents are added, proportions in the range of 0.1 to 10% based on the weight of polysaccharide in the mixture are satisfactory. An important property of the polysaccharide or polysaccharide-emulsifier combination is that when dissolved in water with the polyhydroxy compound, the aqueous phase (a) is capable of emulsifying oil to form the dispersed phase of an oil-in-water emulsion with the oil globules having diameters largely within but not limited to the range of about 0.5 to 5 micron and (b) has sufficient stability not to invert or coalesce prior to moisture removal, e.g., by spray drying.

The polyhydroxy compounds employed in admixture with polysaccharide material in products of the invention are characterized by (a) solubility in water and at least partial solubility in the polysacchride material or capability of at least partially dissolving such material, (b) forming with the polysaccharide material a liquid melt having a softening range at appropriate temperatures with the ranges of proportions used, (c) forming with the polysaccharide material a continuous aqueous phase in which oil is dispersible as a discontinuous phase to form a stable emulsion, (d) plasticity of the surface of the particle formed from the emulsion as water is removed through a drying operation and (e) forming with the polysaccharide material a mixture that is in the solid state at the temperature of use. The useful polyhydroxy compounds can be classified in three groups:

1. Polyhydroxy alcohols, including glycerine, sorbitol, mannitol, erythritol and ribitol.

2. Sugars from plant sources, including monosaccharides such as glucose, disaccharides such as maltose and sucrose, trisaccharides such as raffinose, and ketosaccharides such as fructose. These will be referred to as plant-type sugars whether actually derived from plants or produced synthetically.

3. Polyhydroxy compounds containing other functional groups including glucuronolactone (lactone), sorbitan and mannitan (monoethers) and methylglucopyranoside (acetal).

In general, the proportion of polyhydroxy compounds is at least 20% of the matrix.

The suitability of mixtures of these matrix forming materials, e.g., polysaccharide material (referred to as A) and polyhydroxy compounds (referred to as B) for use in the present invention may be determined by the following test procedures:

1. Solubility Test

A. Dissolve A and B separately in water.

B. Combine the two solutions in proper amounts to give various proportions of A:B on a solids basis over a sufficient range of proportions, in some cases varying the proportions from pure A to pure B, to determine if there are proportions that are useful in the invention.

C. Evaporate water from the mixture, leaving a residue in solid state.

D. Place some of the residue on the hot stage of a microscope and observe the melting behavior as it is heated. If the residue remains essentially homogeneous throughout the softening and molten range, it will be satisfactory for use in the present invention, providing the criteria of the softening range test are met.

2. Softening Temperature Range Test

A. Determine the plastic or softening temperature range of each mixture of A and B, and use these data to construct a simple two component melt diagram for each system as shown in FIGS. 8, 9, 10 and 11 which are typical melting behavior curves for mixtures used in the invention, and which are described in detail hereinafter.

B. The softening, plastic or flowable state of A:B mixture must occur within the temperature range consistent with the drying technique used. It should be noted that the temperature range within which moisture removal occurs, e.g., the temperature of sprayed particles during drying of the emulsion, is not necessarily the same as or overlapping the range determined in 2A, since the melt during moisture removal is a quaternary mixture of A, B, oil and diminishing proportions of water whereas on reheating it is a ternary mixture of A, B, and oil.

The systems of FIGS. 8 – 11 are as follows:

| Fig. | A | B |
|---|---|---|
| 8 | Polysaccharide X | Mannitol |
| 9 | " | Sucrose |
| 10 | " | Sorbitol |
| 11 | Gum Arabic | Mannitol |

The data on melting behavior for these four different combinations of A and B are plotted in FIGS. 8 to 11 in which the ordinate is temperature and the abscissa the present of B in A. In these plots the lower lines connect the temperature of the beginning of softening for the various mixtures and the upper lines connect the temperatures of complete fluidity of each of these mixtures, both of which vary with the proportion of B in A. It will be seen from the plots of temperatures vs. proportions of B in A for the systems shown in FIGS. 8, 9 and 11 that the combinations of ingredients used therein form systems having eutectice within the range of proportions shown whereas the combination used in FIG. 10 does not. The minimum and maximum proportions of A and B that can be used to obtain the benefits of the present invention vary from system to system and are affected also by the oil load. In general the polyhydroxy compound added to the polysaccharide should be at least 20% and in some cases these results are not achieved until considerably more than 20% is present. The effective and optimum proportions of polyhydroxy compound to polysaccharide can readily be ascertained by routine determinations carried out according to the procedures disclosed herein. Products produced from such mixtures have unique technical advantages in that the oil yield and oil contents of the products are a maximum and extractable oil percentages are minimal as illustrated by plots of data of these properties in FIG. 12 for the eutectic composition of FIG. 8.

Visual evidence of the flowability during drying of the compositions of this invention is most clearly obtained from scanning electron microscope photographs of which FIGS. 1, 2, 3 and 4, described more fully hereinafter, are examples. The smooth, rounded nature of the surfaces of spray dried particles of the invention demonstrates that the compositions from which they are derived remain plastic during the drying process. Pits or craters, cracks, fissures, pin holes and like that ordinarily develop during the drying process tend to be prevented or sealed by flow of the plastic combination of materials, thus minimizing the escape of oil both during the drying process and during the lifetime of the resulting solid matrix.

Moisture removal may be carried out over a suitable temperature range by any reasonable process such as vacuum drying, belt drying, slab drying or spray drying; the latter including variations such as water dehydration by a fluent dehydrating agent such as starch. Preferably, the softening temperature range should be such that the material, e.g., particles, remain plastic until almost all of the water has been removed. This softening temperature range should be compatible with the vapor pressure of the material in the dispersed phase.

By extractable oil is meant the oil that is not fixed or stably held within the matrix, e.g., the spray dried particles. A suitable procedure for determination of extractable oil comprises:

1. Agitate at 10 gram sample of the encapsulated product with stirring for 10 minutes in 20 milliliters of trichloromonofluoromethane ($CCl_3F$) at 20°.
2. Filter the sample through a Buchner funnel with gentle vacuum (approximately 10 mm. mercury pressure).
3. Wash the powder with 2 separate 10 ml. portions of $CCl_3F$.
4. Determine the weight of the oil in the solvent. This can be done in any manner that gives dependable results. One way is gently to evaporate the filtrate on a steam bath until the $CCl_3F$ is completely volatilized and weigh the oil residue after evaporation of the solvent, Another way is to read the percentage of oil directly on a properly calibrated wide line nuclear magnetic resonance spectrometer and calculate the extracted oil weight. However determined, the weight of extracted oil is recorded as extractable oil weight.

The percent of extractable oil is calculated from the following expression:

$$\%\ \text{extractable oil} = \frac{\text{extractable oil weight} \times 100}{\text{sample weight}}$$

The stability of the product, i.e., the ability of the product to retain oil or to resist the loss of oil on storage is believed to be related to extractable oil. Product produced in accordance with the invention is stable on storage and has very little extractable oil as may be seen from the curve in FIG. 13 which is a plot of extractable oil versus time for a product of the invention which will be described in detail hereinafter. The extractable oil in this product of the invention is 3.3% at 10 minutes and does not significantly increase with extraction time up to four hours (4.0%). In general, the percentage of extractable oil from particles of the invention at oil levels above 30% is less than 5% in 4 hours. This is in strong contrast to typical prior art products which show much higher extractable oil ranges at the same high oil loadings.

By percent yield is meant the percent ratio of the weight of product removed from the tower to the weight of the ingredients introduced into the tower in the emulsion other than the solvent or vehicle, usually water, i.e., the encapsulating agent and oil.

The oils that can be encapsulated in accordance with the present invention include non-volatile as well as volatile oils such as have been encapsulated by prior methods but the greatest advantages over the prior art are obtained with volatile oils because of the low loss on spray drying, the low extractable oil and high oil recovery. The oils are characterized by being insoluble but dispersible (emulsifiable) in water and they may be volatile or non-volatile under drying conditions which include elevated temperature and low relative humidity in the air stream. They are usually liquid at the temperature of the emulsion but petroleum jelly can be successfully encapsulated by the process of the invention since it is readily broken up into tiny particles in an emulsifying machine producing high shear. Among the volatile oils that can be encapsulated effectively by the present invention are natural and synthetic essential oils or compounded fragrance oils such as citrus (orange, lemon, lime, and the like), spice oils (cascia, clove, wintergreen and the like), mint oils (spearmint, peppermint, and the like), woody oils (vetiver, patchouli, and the like); perfume oils and individual components thereof, such as linalool, methyl salicylate, limonene, menthol, decanol, diethyl phthalate, carvone, citral, and the like; fruit flavors, such as imitation orange, raspberry, apple, banana and individual components thereof, such as benzaldehyde, isoamyl acetate, ethyl butyrate, alpha-ionone, or cis-3-hexenol, and the like; and other imitation flavors or aromas such as nut, meat, vegetable, beverage (such as coffee and tea), condiment, onion, and the like. The oils may also be the carrier for suspended solid particles that may be desirable in the finished product, e.g., fungicides, pigments, and the like.

The proportions of oil to encapsulate or matrix ingredients may vary widely from small but effective amounts to as high as 80% by volume. The principal benefits of the present invention in high yield and low extractable oil are realized in greatest measure where the oil amounts to at least 30% of the composition.

The solvent or vehicle preferably used in the invention to dissolve the polysaccharides and polyhydroxy compounds is water. The viscosity of the emulsion can be modified by varying the proportion of water therein.

Additives may be used in the mixtures of matrix forming ingredients provided the properties described above are not substantially impaired. In some cases the favorable properties of the products are enhanced by the presence of additives. For example, in systems comprising polysaccharide Z having a DE in the range of 10–25 and sucrose at a level within the range of 20% to 60% of the combination of matrix forming ingredients, partial replacement of the polysaccharide by a protein derivative such as sodium caseinate, e.g., up to 50% thereof (i.e., 1 part of polysaccharide Z replaced for each part of sodium caseinate), has no substantial deleterious effect on yield or extractable oil over an oil load range from 15 to 75%. At lower proportions, e.g., 2–10%, sodium caseinate serves as an emulsifying agent, as described above, and at higher levels it also contributes to wall strength and integrity. Other protein derivatives which function similarly are polymers of about 10 to 100 amino acids joined by peptide bonds between the carboxy carbon of one acid and the amino nitrogen of the adjacent acid by elimination of water. A preferred polypeptide is derived from collagen having at least 15% nitrogen (of which 9% is amino nitrogen), 8% maximum water, a maximum ash content after 16 hours at 550°C of 6%, iron less than 5 parts per million (ppm), heavy metals less than 50 ppm, average molecular weight of about 10,000 and a Lovibond color in 1% solution not darker than 2.5 yellow and 0.5 red. The referred proteins are characterized by emulsifying properties in the polysaccharide-polyhydroxy compound system and, at higher proportions, also as contributors to wall strength and particle integrity.

Figure 12:
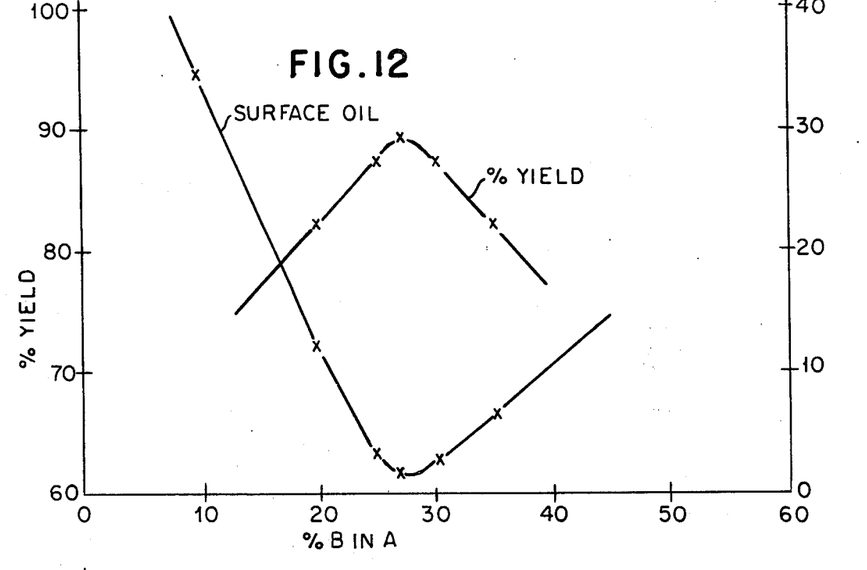
FIG. 12 is a graph showing the melting range, % powder yield and extractable oil at 60% oil loading plotted as ordinates versus % polyhydroxy compound plotted as abscissa for one system of the invention.
Figure 13:
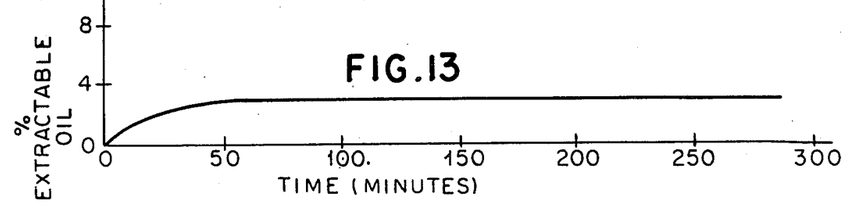
FIG. 13 is a linear plot of % extractable oil versus time for lemon oil in capsules produced by the procedure of the present invention at 45% oil loading.

The mixtures of the polysaccharides and polyhydroxy compounds useful in the invention all satisfy the solubility and softening temperature range tests given above but not all of them exhibit an eutectic within the desired composition range or optimum performance at the eutectic as in the case in the polysaccharide X - mannitor system of FIG. 12. There is, however, a range of proportions of A to B for all satisfactory mixtures which gives a minimum extractable oil content and a maximum yield and this range is easily determined for each mixture of A and B by plotting these values as ordinates for each proportion of B to A as abscissa on graph paper in the manner illustrated in FIG. 12 for the polysaccharide X - mannitol system.

Other satisfactory binary mixtures of A and B include:

| A | B |
| --- | --- |
| Polysaccharide X | Sorbitol |
| '' | Erythritol |
| '' | Fructose |
| '' | Sucrose |
| '' | D-Glucoronolactone |
| '' | Glucose |
| '' | Glycerine |
| '' | Maltose |
| '' | Mannitan |
| '' | Methyl-A-D-Glucopyranoside |
| '' | Raffinose |
| '' | Ribitol |
| '' | Sorbitan |
| Gum Arabic | Fructose |
| '' | Sorbitol |
| '' | Sucrose |
| Polysaccharide Y | Mannitol |
| '' | Sucrose |

A preferred process of making the particulate compositions of the invention comprises dissolving the polysaccharide and polyhydroxy material as defined hereinabove in water, with additions of a surface active material, if necessary, emulsifying the oil in the aqueous phase so as to form a dispersion of droplets having a diameter of the order of about 0.5 to 5 micron, for many purposes preferably about 1 micron, spraying the emulsion into a spray drying tower operating under conditions that will form droplets having the desired diameter, e.g., about fifty (50) microns, removing the moisture content of the droplets to about 2% or less by weight of the resulting solid paraicles by means of the heat and low relative humidity in the drying air, while maintaining the particles at a temperature such that the entire particle, and in particular the surface, remain liquid until the moisture content has attained a low level, e.g., about 5% or so, then solidifying and/or cooling the particles to a glass by evaporation of the remaining few percent of water, or by cooling with air, or both.

In the preferred process the emulsion is prepared in a single vessel equipped with an agitator capable of emulsifying the o/w emulsion to a desired droplet size, e.g., about 1 micron or less. The agitator may be an open blade type or a closed turbine type.

The required quantity of water is placed in the vessel and the solid wall materials are added slowly with agitation. Agitation is continued until solution is complete. The oil is added slowly, e.g., to the vortex produced by the agitator, while the agitator speed is gradually increased to the maximum required. Agitation is continued until the emulsion reaches the required droplet size. Care should be taken not to overheat the emulsion during agitation which could cause rapid coalescence when agitation is stopped. The emulsion may be diluted with an appropriate amount of water to give the desired viscosity. The emulsion is transferred to a holding vessel where it remains with or without agitation as desired until pumped to the dryer.

In the preferred process the emulsion is dried, preferably by spray drying, at temperatures that maintain the particles entirely in a flowable state until nearly all the moisture has been removed. Then the particles are solidified either by cooling or by increasing the solidification point of the mixture by further removal of water, or both, depending on the specifications for the product and the type of equipment being used.

To accomplish moisture removal by spray drying, any suitable spray drying tower may be employed. Typically spray drying towers comprise an upper cylindrical portion where the emulsion to be dried is introduced by rotating discs, nozzles, and the like, and a lower conical portion leading to the product outlet at the bottom of the cone. The drying medium, usually heated air, may be introduced at the top with the emulsion to be dried, the so-called concurrent type, or adjacent to the bottom, the so-called countercurrent type. In general for products of the invention in the form of very fine powders it is preferred to use the concurrent system with centrifugal separation of product from the air after the product has been removed at the bottom of the conical portion of the spray tower. The air used in the drying process is ordinarily taken from the atmosphere and passed over heated surfaces before being introduced into the drying tower. These surfaces may be heated electrically, by flame, by steam, or the like, in accordance with the usual techniques which are understood by those skilled in the spray drying art. Ordinarily the air at the time it is introduced in the tower will have a temperature between about 125° and 300°C but on account of rapid evaporation of the moisture in the emulsion, the heat in the air is absorbed so quickly as latent heat of evaporation that the temperature of the particles from which the moisture is being removed remains within the plastic range throughout the drying operation and the particles then become discrete solids.

Drying may also be effected by spreading a layer of the emulsion on a suitable substrate, e.g., on a heated drum, or on a belt which is then passed through a heating tunnel or subjected to vacuum drying, or on the article where a layer of product is desired and removing moisture therefrom. When drying by means other than a spray tower and on the article where it is desired, it is ordinarily necessary to grind the resultant dried material to the desired particle size. In general spray dried particles ma have a spectrum of sizes up to about 400 microns in diameter but preferably the predominant size for many purposes is about 40 microns in diameter.

The appearance and properties of the products produced by the preferred spray process of the invention are unique and distinct and represent a significant improvement over products produced by spray drying according to the best known commercial techniques in prior use. The unique appearance is readily seen and can be photographed under a scanning electron microscope at various magnifications.

Figure 1:
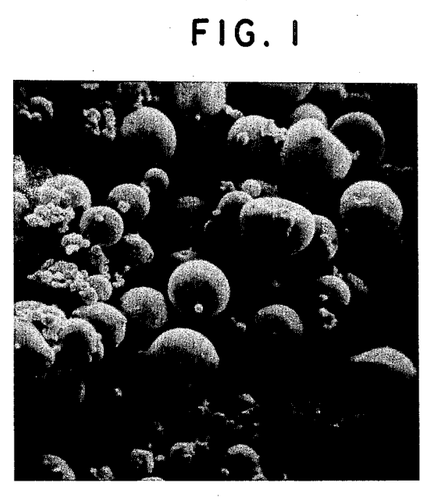
FIG. 1 is an electron photomicrograph of capsules of the present invention at a magnification of 200 diameters.
Figure 2:
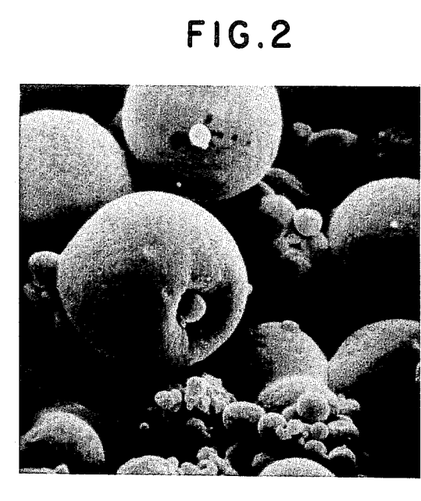
FIG. 2 is an electron photomicrograph of a portion of the same field as FIG. 1 at a magnification of 500 diameters.
Figure 3:
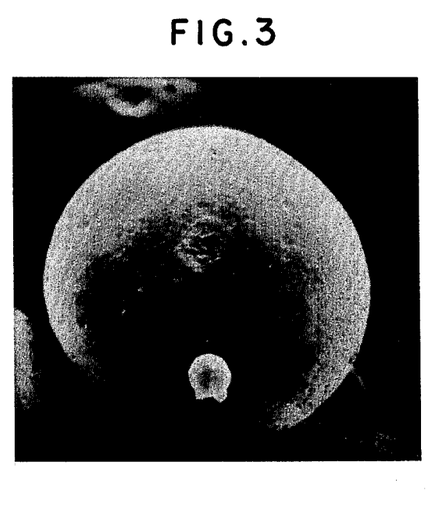
FIG. 3 is an electron photomicrograph of a smaller portion of the same field as FIG. 1 at a magnification of 1000 diameters.
Figure 4:
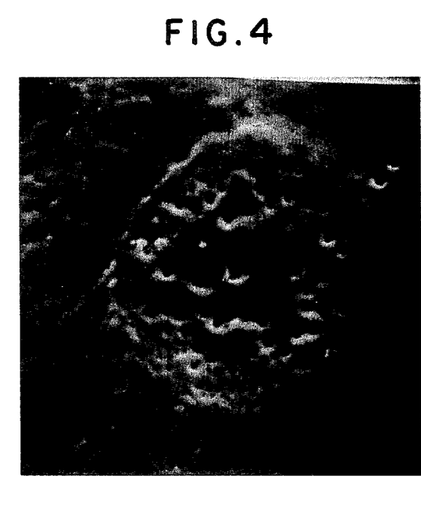
FIG. 4 is an electron photomicrograph of the portion of the surface of the particle in the foreground of FIG. 3 surrounding the disc-shaped area of different texture slightly above the horizontal equator at a magnification of 5000 diameters.

Referring to FIGS. 1, 2, 3 and 4 it will be seen that the product produced in accordance with the present invention is characterized by well defined spherical shape believed to result from the surface tension in the free plastic particles during the drying operation. When one such free plastic particle strikes another there is an infolding of the plastic surface around the striking particle that may hold the two particles together, as may be seen in FIG. 2. As seen in FIG. 1 some of the smaller spherical particles tend to associate in clusters. The surface of all the particles is smooth and glassy and fine pores visible in product produced by prior procedures are absent in the particles of the present invention as shown in FIGS. 1, 2, 3 and 4. The product from which the photomicrographs reproduced in FIGS. 1, 2, 3 and 4 were made was obtained as described in the Example 4e hereafter.

The following examples are given to illustrate the invention but they are not to be considered as limitations on it except as specifically so stated.

EXAMPLE I

A solution of an encapsulant comprising 32 parts glucoronolactone and 48 parts polysaccharide X is prepared by dissolving them in 250 parts of water with agitation at high speed in a household type Waring blender. Single fold orange oil containing 1% butylated hydroxy anisole as antioxidant is slowly added to the resulting solution until 120 parts are incorporated while continuing high speed agitation for 3 minutes, at which time an oil/water emulsion had formed with an average droplet diameter of 0.5 microns. The viscosity as determined with a Brookfield Model LVT Viscometer is 57.5 centipoise at 30°C. The proportions are chosen to give an oil loading of 60% (120 parts oil and 80 parts encapsulant). The mixture is spray dried in a standard Anhydro laboratory drier, size No. 1, maintained at an air inlet temperature of 180°C and an air outlet temperature of 90°C at a feed rate of 3 lbs per hour of emulsion. There is collected 170 parts of powdered product readily passing through a 140 mesh screen which upon analysis by standard steam distillation technique is shown to contain 66% by volume (V/W) or 56% by weight (W/W) of volatile oil based on the weight of the product. This represents an 85% weight recovery of product containing 93% of the theoretical load of orange oil initially employed to make the emulsion. This represents a total recovery of 79% of the original oil. The extractable oil of the product is 0.2% as determined by extraction as described above. The moisture content is 2.1% as determined by Karl Fisher procedure. In general the volatile oil content is determined by the standard steam distillation technique on product as produced. The volatile oil content as so determined includes the extractable oil.

EXAMPLE 2

An emulsion is prepared from 32 parts of sorbitol, 48 parts of gum arabic, 120 parts of an orange oil, 2 parts of sodium di isoocty; sulfosuccinate and 300 parts of water. The resulting emulsion has an average oil particle size of 1.4 microns and a viscosity of 40 centipoise at 30°C. The spray dried powder obtained in a weight yield of 80.3% has 67.4% volatile oil (57.2% by weight, oil factor 0.95) and 0.9% moisture. The product dissolves readily in cold water. Comparable results are obtained using mannitol and sucrose instead of sorbitol.

EXAMPLE 3

Using the same equipment and proceeding in a manner similar to Example 1, 48 parts of sucrose and 32 parts of polysaccharide X are dissolved in 200 parts of water. The viscosity is 35 centipoise at 30°C. To the resulting solution is added 120 parts of cold pressed lemon oil. The resulting emulsion is spray dried with an inlet temperature of 180°C and an outlet temperature of 93°C at a rate of 5 lbs. of emulsion per hour. There is obtained a 95% weight yield of product with a content of volatile oil of 64.7% by volume (55% by weight)

which represents a total recovery of 87.1% of the oil initially used. The extractable oil of the product is 0.6% and the moisture content is 0.23%.

EXAMPLE 4

This example provides a comparison of the results obtained by emulsifying orange oil at five different loads in the same aqueous system containing 2 parts polysaccharide X, 1.2 parts sucrose, 5 parts water and 0.1 part inhibitor and spray drying in substantially the same manner described in Exaples 1 and 3. The five different load levels correspond to about 15, 30, 45, 60 and 75% by weight of oil in. The viscosity of each emulsion was determined before spray drying and the spray dried products were tested and/or analyzed for oil out, powder yield, extractable oil and moisture. The data are tabulated in TABLE I, the actual level of oil in for each product being given in the column of the table having that heading:

TABLE I

| Product | Viscosity CP at T | Powder % Yield | In* | % Volatile Oil Out (V/W) | % Volatile Oil Out(W/W) | % Extractable Oil | % Moisture | Oil Factor** |
|---|---|---|---|---|---|---|---|---|
| a | 17 | 28 | 14.5 | 16.3 | 13.8 | 0.3 | 0.6 | 0.86 |
| b | 18 | 31 | 30.6 | 35.5 | 30.2 | 0.2 | 2.1 | 0.84 |
| c | 66 | 32 | 43.3 | 48.7 | 41.5 | 0.1 | 0.6 | 0.86 |
| d | 23 | 37.5 | 57.5 | 66.9 | 56.8 | 0.9 | 1.0 | 0.89 |
| e | 138 | 32.5 | 72.7 | 81.5 | 69.2 | 3.3 | 0.5 | 0.80 |

*Corrected for volatility and moisture content of solids
**Oil Factor = oil out/oil in, and is corrected for powder yield.

The results of a sieve analysis on each of these five products are recorded in Table II which shows the very desirable quality of the spray dried product.

Table II

| Product | OIL LOAD | | ON 60 | ON 100 | ON 140 | ON 170 | ON 200 | ON 230 | ON 270 | ON 325 | THRU 325 | TOTAL |
|---|---|---|---|---|---|---|---|---|---|---|---|---|
| a | 15% | gm | 0.02 | 0.02 | 0.76 | 1.36 | 4.54 | 4.54 | 0.25 | 17.00 | 9.86 | 38.35 |
|   |     | %  | 0.04 | 0.04 | 1.52 | 2.72 | 9.08 | 9.08 | 0.50 | 34.00 | 19.72 | 76.70 |
| b | 30 % | gm | 0.04 | 0.12 | 0.38 | 1.03 | 5.44 | 4.32 | 0.06 | 17.80 | 14.62 | 43.81 |
|   |     | %  | 0.08 | 0.24 | 0.76 | 2.06 | 10.88 | 8.64 | 0.12 | 35.60 | 29.24 | 87.62 |
| c | 45% | gm | 0.09 | 0.13 | 0.54 | 0.71 | 4.37 | 0.16 | 28.68 | 0.35 | 11.75 | 46.78 |
|   |     | %  | 0.18 | 0.26 | 1.08 | 1.42 | 8.74 | 0.32 | 57.36 | 0.70 | 23.50 | 93.56 |
| d | 60% | gm | 0.15 | 0.15 | 0.32 | 0.48 | 5.42 | 0.25 | 28.50 | 0.56 | 8.96 | 44.79 |
|   |     | %  | 0.30 | 0.30 | 0.64 | 0.96 | 10.84 | 0.50 | 57.00 | 1.12 | 17.92 | 89.58 |
| e | 75% | gm | 0.12 | 0.50 | 1.95 | 6.76 | 20.76 | 3.38 | 0.17 | 9.27 | 0.57 | 43.49 |
|   |     | %  | 0.24 | 1.02 | 3.90 | 13.52 | 41.52 | 6.76 | 0.34 | 18.54 | 1.14 | 86.98 |

Figure 5:
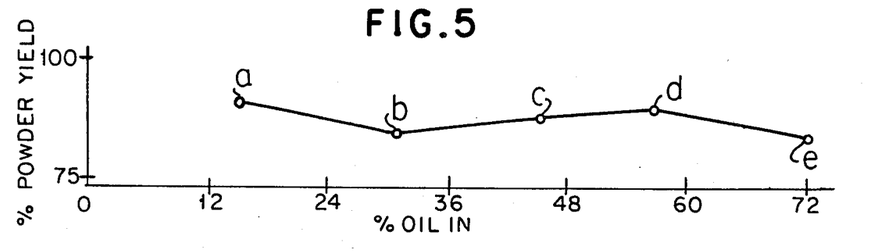
FIG. 5 is a graph of % powder yield versus % theoretical oil load obtained by a typical procedure of the present invention.
Figure 6:
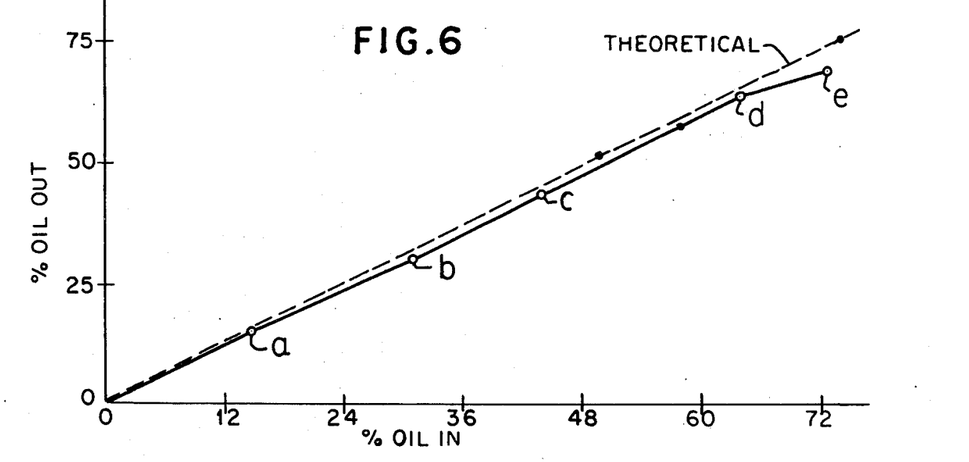
FIG. 6 is a graph of the % oil load actually contained in the capsules versus % theoretical oil load obtained by the same procedure of the present invention.
Figure 7:
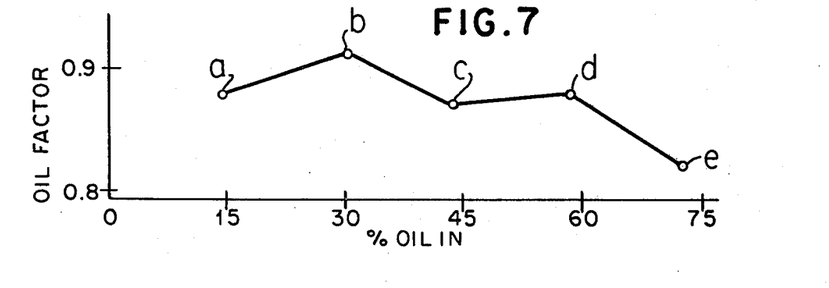
FIG. 7 is a graph of oil factor versus % theoretical oil load, where oil factor is defined as the ratio of total oil recovered to total oil input, obtained by said procedure of the present invention.
Figure 8:
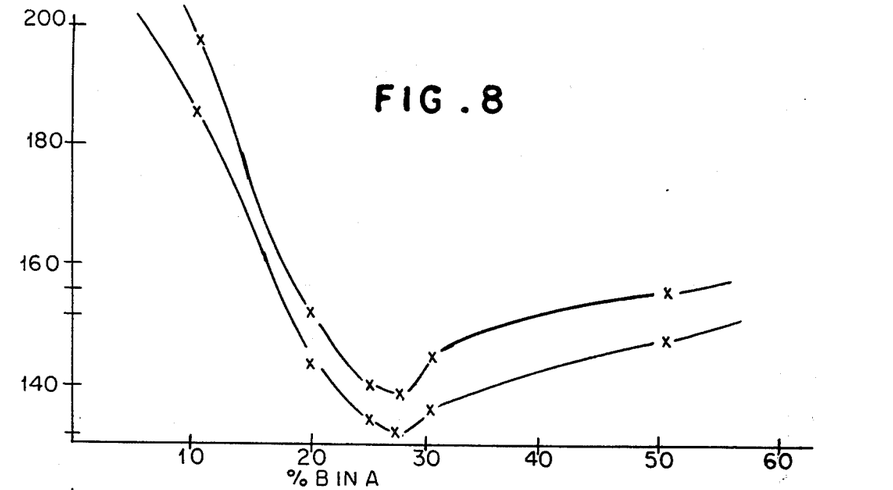
FIGS. 8–11 are graphs of melting behavior of typical two-component systems comprising materials A and B as a function of % B in A.
Figure 9:
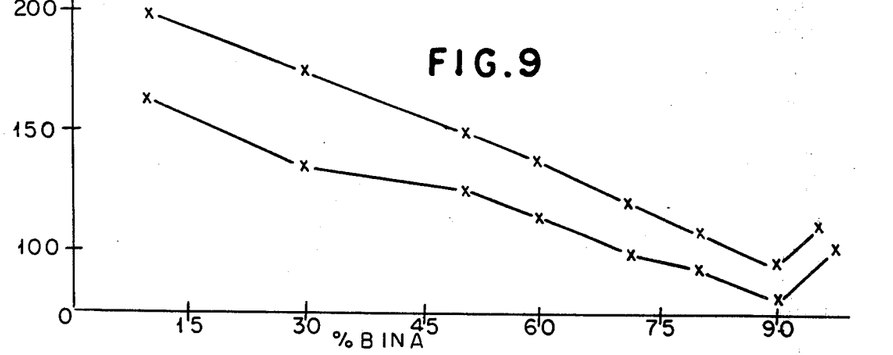
Figure 10:
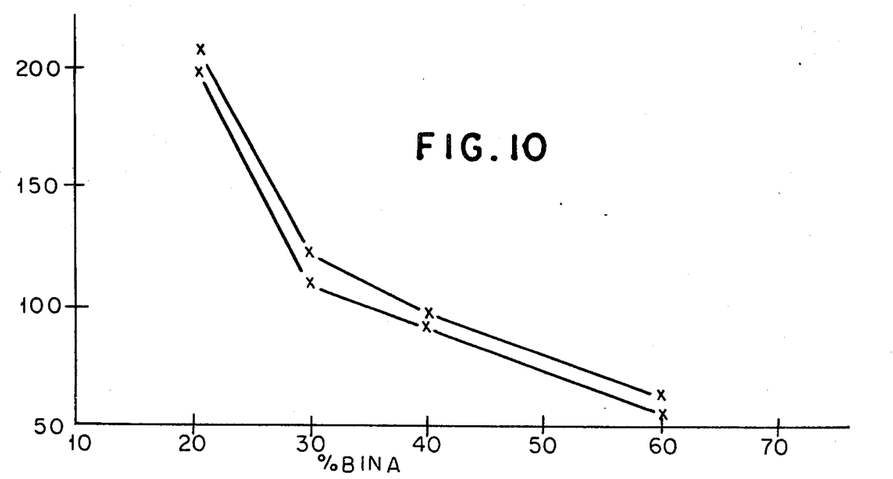
Figure 11:
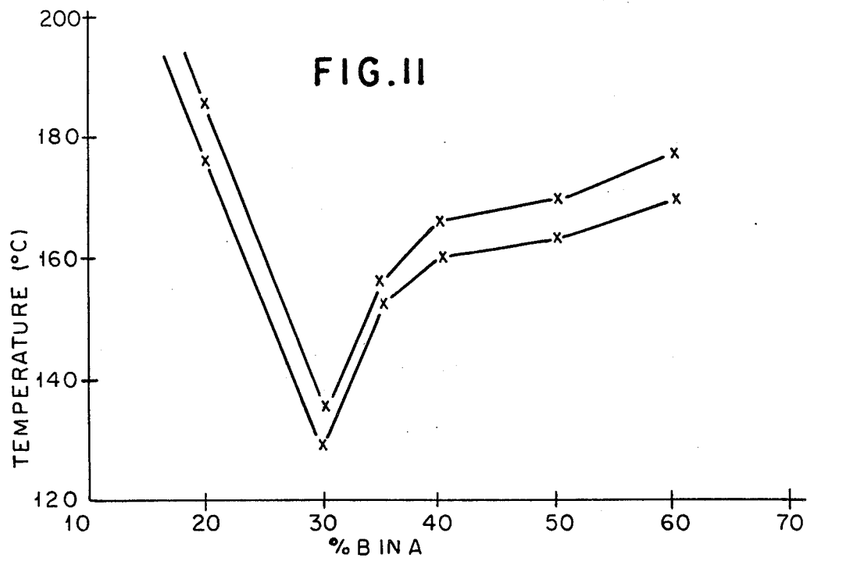

The advantageous results that may be obtained by the present invention are reflected in the physical appearance of the product (FIGS. 1–4) and the combination of high yield of powder (Tables I and FIG. 5) with high oil recovery, particularly at high oil loading (Table I and FIG. 6), low extractable oil (Table I) and the low moisture content (Table I). The photomicrographs in FIGS. 1, 2, 3 and 4, which were taken at the magnifications stated above were made of product e, i.e., the product made in accordance with the process of the invention utilizing the spray drying procedure with approximately maximum theoretical oil load, and show the remarkable absence of cracks, fissures, pin holes and deep pits. Even in the area shown in FIG. 4, which may have been caused by collision with another particle during drying, the evidence of flow is clearly seen that seals the pits close to the surface and provides an excellent oil barrier. FIG. 5 presents graphically the percent yield of powder plotted as ordinate versus percent oil load in an abscissa for products a, b, c, d, and e. FIG. 6 presents graphically the percent oil out as ordinate versus percent oil in as abscissa, for the same products, the dotted line representing the ideal condition representing 100% oil recovery and showing how close the oil recovery in the products of the invention is to the ideal. FIG. 7 presents graphically the oil factor versus percent oil load in for the same products. The significant advantages of the products of the invention, particularly at higher oil loadings, are clear from the photomicrographs and the curves.

EXAMPLE 5

An emulsion is prepared from 27 parts of mannitol, 63 parts of polysaccharide Y, 210 parts of citrus type perfume used for aerosol body deodorant sprays and 300 parts of water. The resulting emulsion has an oil particle size of 1.0 microns and a viscosity of 20 centipoise at 30°C. Spray drying gives an 83% yield of product.

EXAMPLE 6

An emulsion is prepared from 40 parts of mannitol, 80 parts of polysaccharide X, 277.2 parts of diethyl phthalate, 2.8 parts of a leuco dye, and 350 parts of water. The resulting emulsion has an average oil particle size of 1.0 microns, and a viscosity of 30 centipoise at 30°C. Spray drying gives a 93.5% weight yield of product containing 4% extractable oil and 71% by weight of oil. A paper is coated with the fraction of the product that passed through a325 mesh screen by suspending 6.7 parts thereof and 3.3 parts colloidal silica in 100 cc of benzene containing 1 gram of ethyl cellulose and spraying it with an air atomizer onto the paper (compare U.S. Pat. No. 3,179,600 on the coating procedure). The resulting paper is pressure sensitive, releasing its encapsulated dye, for example upon pressure of a ball point pen.

EXAMPLE 7

An emulsion is prepared containing 60 parts of mannitol, 90 parts of polysaccharide Z, 150 parts of polysaccharide X, 300 parts of a pine perfume oil and 700 parts of water. A 91.2% by weight yield of product is obtained by spray drying and passing the product through a 60 mesh screen. The product has 2.3% extractable oil.

EXAMPLE 8

An emulsion was prepared from 60 parts sucrose, 24 parts sodium caseinate, 36 parts polysaccharide Z, 180 parts of cold pressed lemon oil, and 330 parts water. Prior to the addition of the oil, the pH of the emulsion was adjusted to 7, using 20% sodium hydroxide. A 83.8% by weight yield of product was obtained by spray drying and passing the product through a 60 mesh screen. The product has 3.6% extractable oil, and 53.8% by weight total oil.

EXAMPLE 9

An emulsion is prepared from 60 parts of polysaccharide X 30 parts of mannitol, 10 parts of polyvinyl alcohol 325, a product of Airco Chemicals, and 150 parts of an orange oil. The resulting emulsion has an oil particle size of 0.2 microns and a viscosity of 150 centipoise at 30°C, upon spray drying. The product obtained in 87.7% yield contains 65.8% volatile oil, 4.2% extractable oil and 1.2% moisture. This product illustrates the use of two polyhydroxy compounds instead of only one, as in the previous examples, and three or more polyhydroxy compounds may be used if desired. The solubility rate of this product in water is lower than most of the above products, which is desirable for some applications, e.g., bath salts where a prolonged fragrance release is beneficial. The addition of a small proportion of glutaraldehyde to the above described emulsion gives an insoluble product.

EXAMPLE 10

An emulsion was prepared from 40 parts of mannitol, 30 parts of polysaccharide X, 30 parts of polysaccharide Z, and 150 parts of an orange oil. The spray dried product obtained in 81% yield, has a volatile oil content of 63.3%. This product shows that two polysaccharides may be used instead of one, as in the previous examples. Comparable results are obtained by using three and more polysaccharides in suitable proportions.

EXAMPLE 11

Additional polyhydroxy compounds (PHC) which may be employed in preparing emulsions with polysaccharide X (PSX), orange oil and water are listed in Table III which gives suitable proportions and the percentage of volatile oil in the resulting products produced by spray drying in accordance with Example 1:

TABLE III

| Product | PHC and Parts | Parts PSX | Parts Orange Oil | % Volatile Oil V/W |
|---|---|---|---|---|
| f | Mannitan 20 | 80 | 150 | 58. |
| g | Sorbitan 20 | 60 | 120 | 62.5 |
| h | Glucose 40 | 40 | 120 | 66.7 |
| i | Maltose 60 | 40 | 150 | 54. |
| j | Raffinose 70 | 30 | 150 | 58. |
| k | Fructose 45 | 55 | 150 | 61. |
| l | Glycerine 30 | 70 | 150 | 60. |
| m | Erythritol 30 | 70 | 150 | 61. |
| n | Methyl-alpha-Glucopyranoside 40 | 40 | 120 | 63.3 |
| o | Dulcitol 30 | 70 | 150 | 60. |

EXAMPLE 12

Petroleum jelly is emulsified in an open blade mixer in an aqueous solution of polysaccharide X and mannitol until the particle size of the jelly droplets is in the range of 2–4 microns. The viscosity of the emulsion is 94.5 cp at 33°. It is sprayed at 27° into a drying tower in a manner similar to Example 1. The product yield is 73%.

EXAMPLE 13

An oil dispersible F.D. & C. dye, red No. 37, at 1% in oil (Wickenol 161) is emulsified in an aqueous solution of polysaccharide X and mannitol at a 60% load level. The viscosity of the emulsion at 25° is 76 cp. The product is obtained on spray drying in a manner similar to Example 1 in 87% yield. It is pinkish-red in color.

EXAMPLE 14

A water dispersible F.D. & C. dye, blue No. 1, at 1% in vegetable oil is emulsified in an aqueous solution of polysaccharide X and mannitol. The emulsion has a viscosity at 26° of 43 cp and is spray dried in a manner similar to Example 1. A yield of 89% of blue capsules is obtained which contain the water dispersible dye. On contact with water the color is readily dispersed therein.

The emulsions produced in the manner described herein normally have a pH value within the range of about 4 to 6. If additives are present in an amount to change the normal pH substantially, extractable oil in the product may increase. In the event that this phenomenon should occur in practice of this invention, the addition of a suitable acid or base to the emulsion may be indicated to adjust the pH to a value within the range of 4 to 6.

The benefits and advantages of the product and process of the invention over products currently available commercially and the process of producing the same are many, among which are the following:

| Invention | Prior Art |
|---|---|
| 1. High oil factor (proportion of oil out to oil in) in the product at all oil levels, e.g., over 0.8 up to 73% orange oil in. | 1. Low proportion of oil in products having an oil factor over 0.8, e.g., not over about 30% orange oil. |
| 2. Extractable oil below 1% at oil contents up to 60% by volume and only slightly higher at 73%. | 2. Extractable oil up to 12% at oil contents up to 60% by volume. |
| 3. Moisture content typically under 1%. | 3. Moisture content typically 3% and higher. |
| 4. Top notes of citrus excellent (stability on storage). | 4. Top notes of citrus somewhat terpeney (on storage). |
| 5. Smooth spheres. | 5. Wrinkled or cracked spheres. |
| 6. Glassy cellular matrix free of surface porosity. | 6. Porous surface. |

The powders produced by spray drying in accordance with the invention are free-flowing, e.g., about 98% passing readily through a 140 mesh screen for oil loadings up to 60% and by proper choice of matrix ingredients may vary in solubility in water from instant solubility to practically insoluble. Other mesh sizes are also readily prepared.

The particulate compositions of the invention can be used in all products in which particulate compositions of the prior art have been used, such as foods, beverages, cosmetics, paper products, detergents, chemical specialties and the like. In addition the perfume or flavor oils may contain ingredients soluble or suspended in then such as are used in cosmetics, foods, pharmaceuticals and toxicology, e.g., dyes, pigments, vitamins, preservatives, drugs, fungicides and the like.

The following is a partial list of both flavor and fragrance type applications for the invention described herein:

FRAGRANCE

Cosmetics:

Facial scrubs, body powders, face powders, lipstick, depilatory powders.

Toiletries:

Dusting powders, bath oils, body oils, bubble bath powders, bath salts.

Personal Care:

Anti-perspirants, body sprays, foot spray, hygiene sprays (all aerosol and non-aerosol), baby diaper sprays, dry shampoos, deodorant body powders, feminine napkin sprays, undergarment sprays (for girdles, etc.), mouth washes.

Household Products:

Powdered detergents, cleansers (chlorinated and nonchlorinated), scouring powders, powdered soaps, room deodorants.

Paper Products:

Disposable baby diapers, disposable bed linens, feminine napkins, tampons, shoe liner inserts, end papers (for use with cold wave lotions and dyes), paper towels, tissues, carbon-less carbon paper, typewriter ribbon (ink, with or without fragrance).

Snack Foods:
Extruded, cooked, baked.

Desserts:
Canned, mixes.

Baked Products:
Cake mixes, cookies, dough.

Seasonings and Garnishings

Synthetic Food Analogs
Dry mixes and concentrates.

Pet Foods:
Canned, dry, intermediate moisture.

Miscellaneous Chemical:

Incense, room deodorant blocks, solvents, fuels, monomers, lubricants, catalysts, inks, detergents, explosives, drilling fluids, fungicides, pesticides, insecticides, insect repellants, pheromones, waxes, medicinals, biologicals, colloids, and the like.

The product of the invention can be prepared by drying procedures other than spraying, e.g., by drying on belts, drums, and like surfaces from which the product is removed and may be ground to desired particle size. Particles produced in this manner will not have the appearance of the particles shown in FIGS. 1, 2, 3 and 4 but, if made from ingredients that yield such products on spraying, have many of the novel features and advantages of them. In some instances it is not necessary to prepare the product in particulate form for use, e.g., a paper or plastic cup or other container can be coated internally with a layer of appropriate thickness of the emulsion prepared in accordance with this invention containing mouth wash ingredients and then dried. The mouth wash is then prepared for use simply by filling the cup with water. Similarly carbon-less carbon paper may be prepared by coating directly with the emulsion and drying.

The specific examples are illustrative of the invention and are not to be considered as limiting with respect to the ingredients, proportions, process conditions or as to equipment than can be used for making the particulate composition of the invention. In all cases temperatures are given in degrees centigrade and proportions are by weight unless specified to be by volume. Modifications and variations may be made within the principles and ranges specified above and set forth in the claims.

Having thus described, illustrated and exemplified the invention, what is claimed is:

1. The process of encapsulating an oil in a solid matrix comprising a mixture of a modified starch derived from ungelatinized starch acid esters of substituted dicarboxylic acids represented by the formula:

in which R is a radical selected from the group consisting of dimethylene and trimethylene and $R_1$ is a hydrocarbon selected from the class consisting of alkyl, alkenyl, aralkyl and aralkenyl groups and a polyhydroxy compound present in an amount at least 20% of the mixture and selected from the group consisting of alcohols, plant-type sugars, lactones, monoethers and acetals, which process comprises forming a solution of the modified starch and the polyhydroxy compound in water, emulsifying the oil in said solution and spray drying said emulsion to remove water therefrom.

2. The process of encapsulating an oil in a solid matrix comprising a mixture of a hydrolyzed starch and a polyhydroxy compound present in an amount at least 20% of the mixture and selected from the group consisting of alcohols, plant-type sugars, lactones, monoethers and acetals which comprises forming a solution of the modified starch and the polyhydroxy compound in water, emulsifying the oil in said solution and spray drying said emulsion to remove water therefrom.

3. A composition consisting essentially of a water-soluble cellular matrix of hydrolyzed starch and at least one other polyhydroxy compound and having globules of oil in the cells thereof, said other polyhydroxy compound being at least about 20% of the matrix by weight and being a water-soluble member selected from the class consisting of alcohols, plant-type sugars, lactones, monoethers and acetals said composition having been produced by the process of claim 49.

4. A composition according to claim 3 in which the polyhydroxy compound is mannitol.

5. A composition according to claim 3 in which the polyhydroxy compound is sorbitol.

6. A composition consisting essentially of a water-soluble matrix of modified starch derived from ungelatinized starch acid esters of substituted dicarboxylic acids represented by the formula in which R is a radical selected from the group consisting of dimethylene and trimethylene and $R_1$ is a hydrocarbon selected from the class consisting of alkyl, alkenyl, aralkyl and aralkenyl groups and at least one other polyhydroxy compound and having globules of oil in the cells thereof, said other polyhydroxy compound being at least about 20% of the matrix by weight and being a water-soluble member selected from the class consisting of alcohols, plant-type sugars, lactones, monoethers and acetals said composition having been produced by the process of claim 48.

7. A composition according to claim 6 in which the polyhydroxy compound is mannitol.

8. A composition according to claim 6 in which the polyhydroxy compound is sorbitol.

9. A composition according to claim 3 in which the oil is a perfume oil.

10. A composition according to claim 3 in which the oil is a flavor oil.

11. A composition according to claim 4 in which the oil is a perfume oil.

12. A composition according to claim 4 in which the oil is a flavor oil.

* * * * *